(12) United States Patent
Pavesio et al.

(10) Patent No.: US 7,968,111 B2
(45) Date of Patent: Jun. 28, 2011

(54) GRAFTS FOR THE REPAIR OF OSTEOCHONDRAL DEFECTS

(75) Inventors: Alessandra Pavesio, Padua (IT); Lanfranco Callegaro, Thiene (IT)

(73) Assignee: Fidia Advanced Biopolymers S.r.L., Abano Terme (IT)

( * ) Notice: Subject to any disclaimer, the term of this patent is extended or adjusted under 35 U.S.C. 154(b) by 1170 days.

(21) Appl. No.: 10/467,142

(22) PCT Filed: Feb. 6, 2002

(86) PCT No.: PCT/EP02/01224
§ 371 (c)(1),
(2), (4) Date: Aug. 4, 2003

(87) PCT Pub. No.: WO02/070030
PCT Pub. Date: Sep. 12, 2002

(65) Prior Publication Data
US 2004/0076656 A1    Apr. 22, 2004

(30) Foreign Application Priority Data
Feb. 9, 2001    (IT) .............................. PD2001A0032

(51) Int. Cl.
*A61F 2/00*    (2006.01)
(52) U.S. Cl. ..................................... 424/426; 623/16.11
(58) Field of Classification Search .................. 424/422, 424/93.7; 435/325, 372, 395
See application file for complete search history.

(56) References Cited

U.S. PATENT DOCUMENTS 5,631,011 A * 5/1997 Wadstrom ..................... 424/400
5,939,323 A * 8/1999 Valentini et al. ............. 435/395

FOREIGN PATENT DOCUMENTS

| WO | WO 93/30858 A | 10/1993 |
|----|---------------|---------|
| WO | WO 94/17837 A | 8/1994 |
| WO | WO 99/61080 A | 12/1999 |
| WO | WO 99/65534 A | 12/1999 |
| WO | WO 00/01733 A | 1/2000 |
| WO | WO 00/37124 A | 6/2000 |
| WO | WO 00/61675 A | 10/2000 |

OTHER PUBLICATIONS

Caplan A.I. Commentary: Tissue engineering designs for the future: New logics, old molecules, Tissue Engineering, 2000, vol. 6, No. 1, pp. 1-8, entire document.*
Caplan A.I. "Tissue Engineering designs for the future: new logics, old molecules", Tissue Engineering, 2000, vol. 6, No. 1, pp. 1-8, entire document.*
Gao et al., Tissue Engineering (2001), 7(4), pp. 363-371, Aug. 2001.
Bakos et al., Biomaterials, Elsevier Science Publishers BV., Barking, GB, vol. 20, No. 2, Jan. 1999, pp. 191-195.
Burg et al., Biomaterials, Elsevier Science Publishers BV., Barking, GB, vol. 21, No. 23, Dec. 1, 2000, pp. 2347-2359.

* cited by examiner

*Primary Examiner* — Jon P Weber
*Assistant Examiner* — Satyendra K Singh
(74) *Attorney, Agent, or Firm* — Birch, Stewart, Kolasch & Birch, LLP

(57) ABSTRACT

The invention concerns the preparation and use of a biocompatible, biocomponent material constituted by: (a) a three-dimensional matrix of hyaluronic acid derivatives witle a structure containing empty spaces; (b) a porous, three-dimensional matrix constituted by a ceramic material; (c) possibly containing pharmacologically or biologically active ingredients.

28 Claims, 1 Drawing Sheet

Figure 1B:
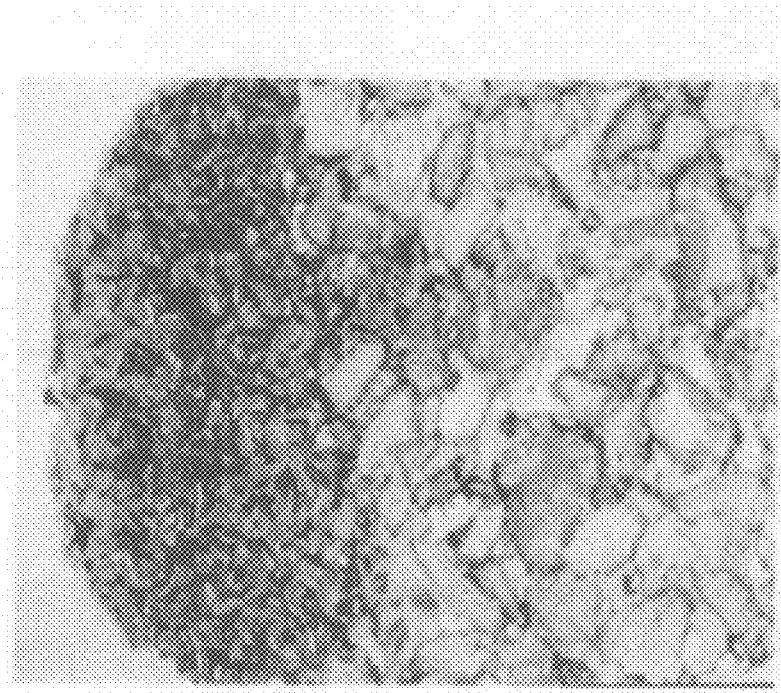

(1 of 1 Drawing Sheet(s) Filed in Color)

GRAFTS FOR THE REPAIR OF OSTEOCHONDRAL DEFECTS

This application is the national phase under 35 U.S.C. §371 of PCT International Application No. PCT/EP02/01224 which has an International filing date of Feb. 6, 2002, which designated the United States of America.

SUBJECT OF THE INVENTION

The present invention concerns the preparation and use of a biocompatible, bicomponent material constituted by:
a. a three-dimensional matrix of hyaluronic acid derivatives with a structure that contains empty spaces created by communicating pores and/or a tangle of fine fibres or microfibres and;
b. a porous, three-dimensional matrix constituted by a ceramic material or by a composite material containing at least one ceramic material;
c. and possibly containing pharmacologically or biologically active ingredients;

for the preparation of engineered, osteochondral grafts containing a cartilage part and a bony part, separate but structurally integrated, using osteochondrogenic cells and for the repair/regeneration in vivo of structurally integrated osteochondral tissue.

BACKGROUND OF THE INVENTION

The loss of osteochondral tissue from the joints following extensive arthritis, necrosis or as a result of a trauma or the removal of a tumour requires reconstructive surgery to repair the defect.

The treatment of such defects by means of joint replacements is limited by the fact that the non-biological materials used are prone to wear and tear, and that the replacements themselves may be difficult to move.

Alternatively, it is possible to resort to autologous, allogeneic or xenogeneic bone grafts. The ideal way of substituting bone is by grafting autologous tissue, which has a better osteogenic capacity than allografts and xenografts, as shown by the presence, during its resorption, of mesenchymal cells that differentiate into osteogenic and chondrogenic cell lines (K. L. B. Brown et al., Surg. 1982, 64A, 270-279). Moreover, allografts and xenografts carry antigens of histocompatibility, making it necessary to administer immunosuppressive treatment to the patient, while autografts do not trigger any immunological response. Besides this, there is the possibility that allografts and xenografts may transmit viruses to the recipient, such as HIV, hepatitis or BSE.

Since bone autografts cause a second trauma to the patient when the graft is taken from the donor site, and because of the paucity of available tissue, the use of this procedure is rather limited.

Orthopaedic research has long been focused on the study of new, artificial materials suitable for osteochondral grafts which would reduce or eliminate the need to resort to tissue grafts.

In order to meet requirements, a material must be biocompatible, bioresorbable at a rate that is comparable to bone growth, able to bear load, be easy to sterilise and process, be osteoactive, that is, it must be an osteoinductor, to induce mesenchymal cell differentiation into bone progenitor cells, and an osteoconductor, to enable the growth of bone within the graft.

The techniques reported in the literature for bone regeneration refer to the use of ceramics, polymers, composite materials and bioactive molecules.

The fact that, from a chemical and structural point of view, calcium phosphates are similar to the mineral part of bone that is mainly constituted by biological hydroxyapatites, has promoted the use of ceramics as biomaterials to induce osteogenesis.

The ceramics most commonly used are beta-tricalcium phosphate (TCP) and synthetic hydroxyapatite. They have proved to be osteoconductors, thanks to their porosity that favours cell colonisation and bone growth.

Studies conducted with subcutaneous implants in syngeneic rats have shown that the combination of bone marrow cells and porous ceramics promote osteogenesis, with the formation of new bone within the pores. Moreover, small, isolated areas of cartilage without any appreciable endochondral ossification have been observed (H. Ohgushi et al., J. Orthop. Res., 1989, 4, 568-578).

The widespread use of polymers is explained by the possibility of obtaining different compositions and structures able to satisfy the requirements of the specific applications as well as the property of biodegradation. It is known that poly-lactic acid, polyglycolic acid and copolymers or derivatives thereof can be used, in various forms, as biomaterials for the growth of osteocytes. The main disadvantage of using such scaffolds is represented by the immune response directed against the implanted material.

In order to create a biomaterial that is satisfactory both from a mechanical and biological point of view, various composite materials formed by mixtures of polymers and calcium phosphates have been investigated.

It is also known that scaffolds containing at least one hyaluronic acid derivative can be used as biomaterials for tissue growth.

Hyaluronic acid is a polysaccharide ether composed of alternate residues of D-glucuronic acid and N-acetyl-glucosamine. It is a linear polymer chain with a molecular weight that varies between 50,000 and 13,000,000 Da, depending on its source and on the methods of preparation and determination that are used. It is present in nature in the pericellular gels, in the fundamental substance of the connective tissue of vertebrate organisms of which it is the main component, in the synovial fluid of joints, in the vitreous humor, in human umbilical cord and in rooster combs.

Hyaluronic acid plays a vital role in many biological processes such as hydration, proteoglycan organisation, cell differentiation, proliferation and angiogenesis (J. Aiger et al., L. Biomed. Mater. Res. 1998, 42, 172-181).

It is also known that hyaluronic acid fractions can be used to enhance tissue repair, to substitute the intraocular fluid, or they can be administered by the intra-articular route to treat joint pathologies, as described in European patents No.s 0138572 and 0535200.

Hyaluronic acid plays a fundamental role in the tissue repair process, especially in the early granulation stage, stabilising the coagulation matrix and controlling its degradation, favouring the recruitment of cells involved in the inflammatory process, such as fibroblasts and endothelial cells and, lastly, orienting the subsequent migration of epithelial cells.

It is known that the application of hyaluronic acid solutions can accelerate the tissue repair process in patients with wounds or burns. The role of hyaluronic acid in the various phases of the tissue repair process has been described by the construction of a theoretical model by P. H. Weigel et al., J. Theor. Biol., 119:219, 1986.

The use of low-molecular-weight fractions of hyaluronic acid and the autocrosslinked derivatives thereof is also known in the preparation of pharmaceutical compounds that are osteoinductors (WO 93/20827).

The total or partial esters of hyaluronic acid (HYAFF®) and its autocrosslinked derivatives (ACP®) are known, as is their use in the pharmaceutical and cosmetic fields and in that of biodegradable materials (U.S. Pat. Nos. 4,851,521; 4,965,353 and 5,676,964).

In particular, patent application No. WO 93/20858 describes binding solutions and pastes containing hyaluronic acid and/or the ester derivatives thereof used as bone fillers in surgery.

Lastly, esters of hyaluronic acid have been processed in the form of non-woven structures according to the process described in U.S. Pat. No. 5,520,916.

Hyaluronic acid derivatives in three-dimensional form and, in particular, partial and total esters of hyaluronic acid (HYAFF®) processed in the form of non-woven tissues have been used as scaffolds in the preparation of biological materials containing cells and/or products generated from such cells.

For example, it has recently investigated the possibility of using the benzyl ester of hyaluronic acid (HYAFF®-11) as a scaffold, in a form of a non-woven fiber structure, for the culture of human chondrocytes in tissue-engineering procedures of cartilage reconstruction. In these 3D cultures, chondrocytes were able to produce hyaline cartilage-specific matrix molecules like collagen type II or proteoglycans, (J. Aiger et al., L. Biomed. Mater. Res. 1998, 42, 172-181).

We can, moreover, mention patent application No. WO 97/18842 that describes a material containing:
  a. an efficient culture of autologous or homologous stem cells from bone marrow, partially or completely differentiated into cells of a specific connective tissue, containing moreover the matrix secreted by said cells, or alternatively,
  a'. the extra-cellular matrix secreted by completely or partially differentiated bone marrow stem cells or, alternatively, by mature cells of the tissue;
  b. a three-dimensional matrix consisting of hyaluronic acid derivatives and, in particular, partial or total esters (HYAFF®).

Hyaluronic acid derivatives in the form of sponges (HYAFF®-11 sponge, made of benzyl ester of hyaluronic acid, and ACP® sponge, made of cross-linked hyaluronic acid) used in combination with mesenchymal cells, implanted subcutaneously in nude mice, have exhibited a better osteogenic and chondrogenic capacity in terms of quantity of tissue formed, than porous ceramics (L. A. Solchaga et al., J. Orthop. Res., 17, 1999, 205-213).

In another experiment, the above said two hyaluronan derivatives-based biomaterials were tested for their ability to enhance the natural healing response of the articular cartilage for self-repair. The introduction of these polymers into osteochondral defects (made on the femoral condyles of rabbits) provides an appropriate scaffolding for the reparative process: in fact, the defects treated with HYAFF®-11 and ACP® sponges exhibited good bone fill and the surface of the condyles was mainly constituted of hyaline cartilage. (L. A. Solchaga et al., J. Orthop. Res., 18, 2000, 773-780).

It has proved extremely important to guarantee the development of a stable interface between the joint cartilage and underlying bone structure when repairing osteochondral defects.

Composite materials constituted by engineered cartilage stitched over an osteoconductor biomaterial scaffold, for the regeneration of osteochondral tissue have been implanted in defects created in rabbit joints. Six months later, it was possible to observe the remodelling of the composite material into an osteochondral tissue structurally similar to the natural variety, with a clear tidemark between the cartilage and the subchondral bone (D. Schaefer et al., $4^{th}$ Annual Meeting of the Orthopaedic Research Society, 2000).

Therefore, although the use of hyaluronic acid derivatives and ceramic materials was already known both for the regeneration/repair of cartilage and bone and as scaffolds for the culture of differentiated and non-differentiated cells, and that an expert in the field could, consequently, have deduced that it was possible to use either of these materials to make osteochondral grafts, it could not have been foreseen, as demonstrated by the present invention, that once the two materials had been coupled, it would be possible to obtain separate formations of cartilage and bone that are structurally integrated but with no penetration between the tissues, like natural osteochondral tissue.

BRIEF SUMMARY OF THE INVENTION

The present invention concerns the preparation and use of a biocompatible, bicomponent material constituted by:
  a. a three-dimensional matrix of hyaluronic acid derivatives, with a structure containing spaces created by communicating pores and/or a tangle of fine fibres or microfibres;
  b. a porous three-dimensional matrix, constituted by a ceramic material or a composite material containing at least one ceramic material;
  for the preparation of structurally integrated, engineered, osteochondral grafts using osteochondrogenic cells and for the regeneration/repair of osteochondral tissue in vivo.

A further subject of the present invention is the use of the composite biomaterial as described above for the repair/regeneration of osteochondral defects, obtained by the coupling of a hyaluronic acid derivative and another material, that may be a ceramic or a derivative thereof or another component with osteoactive properties. It is possible to use said composite material in association with osteogenic cells for the preparation of engineered, osteochondral tissue.

BRIEF DESCRIPTION OF THE DRAWING(S)

The patent or application file contains at least one drawing executed in color. Copies of this patent or patent application publication with color drawing(s) will be provided by the Office upon request and payment of the necessary fee.

Figure 1A:
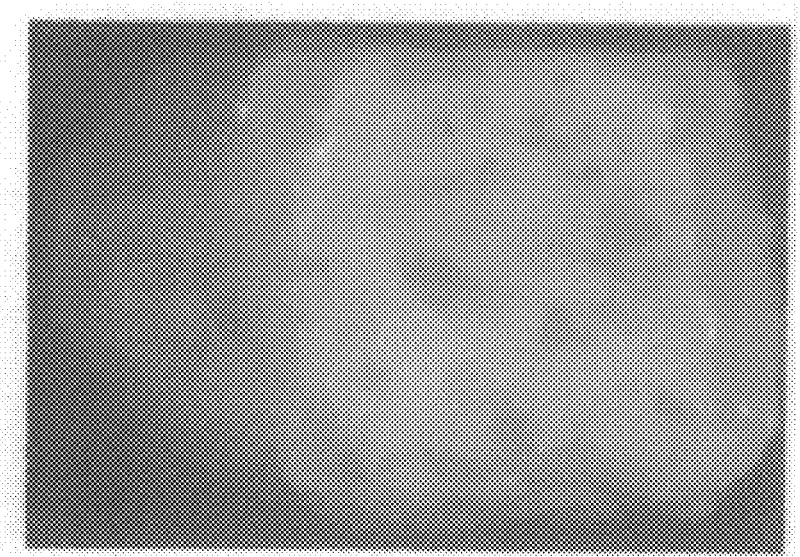

FIG. 1: gross appearance (FIG. 1a) and histology section (FIG. 1b, stained with toluidine blue x 4) of a sample taken 6 weeks after grafting.

DETAILED DESCRIPTION OF THE INVENTION

The present invention concerns the preparation and use of a biocompatible, bicomponent material constituted by:
  a. a three-dimensional matrix of hyaluronic acid derivatives, with a structure containing spaces created by communicating pores and/or a tangle of fine fibres or microfibres;
  b. a porous three-dimensional matrix, constituted by a ceramic material or a composite material containing at least one ceramic material;

for the preparation of structurally integrated, engineered, osteochondral grafts using osteochondrogenic cells and for the regeneration/repair of osteochondral tissue in vivo.

A further subject of the present invention is the use of the composite biomaterial as described above for the repair/regeneration of osteochondral defects, obtained by the coupling of a hyaluronic acid derivative and another material, that may be a ceramic or a derivative thereof or another component with osteoactive properties. It is possible to use said composite material in association with osteogenic cells for the preparation of engineered, osteochondral tissue.

The hyaluronic acid derivatives used in the three-dimensional scaffold (A) are chosen from the following group:
  hyaluronic acid esters wherein part or all of the carboxy functions are esterified with alcohols of the aliphatic, aromatic, arylaliphatic, cycloaliphatic or heterocyclic series (EP 0216453 B1);
  autocrosslinked esters of hyaluronic acid wherein part or all of the carboxy groups are esterified with alcoholic functions of the same polysaccharide chain or of other chains (EP 0341745 B1);
  autocrosslinked composite materials of hyaluronic acid wherein part or all of the carboxy groups are esterified with polyalcohols of the aliphatic, aromatic, arylaliphatic or heterocyclic series, generating crosslinking by means of spacer chains (EP 0265116 B1);
  hemiesters of succinic acid or heavy metal salts of the hemiester of succinic acid with hyaluronic acid or with partial or total esters of hyaluronic acid (WO 96/357207);
  O-sulphated derivatives (WO 95/25751) or N-sulphated derivatives (WO 98/45335);
  amides of hyaluronic acid or of its derivatives (WO 00/01733).

The hyaluronic acid derivatives may be in the form of non-woven fabrics, membranes, sponges. Said hyaluronic acid derivatives may in turn include pharmacologically or biologically active substances.

The porous three-dimensional matrix, as per point B, may be constituted by:
  hydroxyapatite or other calcium phosphates, including tricalcium phosphate;
  calcium sulphates;
  a composite material constituted by hydroxyapatite and tricalcium phosphate;
  a composite material constituted by:
    a) hydroxyapatite or other calcium phosphates or calcium sulphates;
    b) other biocompatible ceramics, metal particles or polymers;
  a ceramic material coated with hydroxyapatite or other calcium phosphates, including tricalcium phosphate;
  bioactive glass.

Said materials may in turn include pharmacologically or biologically active substances.

The pharmacologically active substances of choice are antibiotics, disinfectants and antiseptics, antiviral, antimicrobic and antifungal agents, nonsteroid and steroid anti-inflammatory drugs, cytostatic, cytotoxic, anaesthetic and anticancer agents.

Of the biologically active substances, we should mention those that favour the adhesion of cells to the biomaterial, such as fibronectin, "RGD" or integrin sequences, growth factors such as "transforming growth factor beta" (TGF-beta), insulin-like growth factor (IGF), epidermal growth factor (EGF), acid or basic fibroblast growth factor (aFBF or bFBF), hepatocyte growth factor (HGF), keratinocyte growth factor, bone morphogenic proteins (BMPs) such as BMP-1, BMP-2, BMP-3, BMP-4, BMP-5, BMP-6, osteogenic proteins (Ops) such as OP-1, OP-2, OP-3, growth proteins, vitamins such as vitamins C, D, E and other natural substances such as glucosamine sulphate.

The various three-dimensional matrices that constitute the components of the composite biomaterials for osteochondral grafts are assembled with the aid of a natural, synthetic or semi-synthetic, biocompatible, preferably absorbable glue, that is sufficiently adhesive. For example, it is possible to use a fibrin glue of biological origin that is widely used in clinical practice and has proved to be suitable and effective for this purpose.

Alternatively, should the materials of the various three-dimensional matrices that constitute the components of the composite biomaterial allow it, it is possible to join them by suture or with items such as screws or nails, as used in health care and surgery.

Once the composite, bicomponent material is ready, it can be grafted into the site of the defect as it is, without any cellular components or products thereof, to act as a supporting structure in the regeneration/repair of osteochondral tissue in vivo.

Alternatively, said composite material may contain suitably inoculated differentiated or non-differentiated cells and can be used as a scaffold in which to grow said cells before grafting.

Moreover, it is possible to assemble the aforesaid two components after osteochondrogenic cells have been inoculated into them. In particular, the three-dimensional scaffold constituted by a hyaluronic acid derivative may be loaded with progenitor cells or with mature chondrocytes in order to repair/regenerate the cartilage tissue. The three-dimensional, porous matrix can be used as a scaffold for the culture of mesenchymal cells or mature bone cells in order to repair/regenerate bone.

Example of the Preparation of the Osteochondral Graft
Cell Culture

It is known from the literature that progenitor, osteochondral cells known as mesenchymal stem cells (MSCs) also differentiate into chondrocytes and osteocytes.

In the case of the present invention, mesenchymal stem cells were isolated from rat bone marrow and grown and expanded according to the protocol that appears in the literature (Lennon et al., In vitro Cell Devel. Biolo., 1996, 32, 602-611).

When the primary cells have reached confluence, they are detached from the dish by enzymatic treatment and expanded to obtain different preparations for use in different conditions.

To favour the differentiation of the mesenchymal stem cells along the chondrocyte line, they are grown in the presence of TGF-beta 1 at 10 ng/ml. To favour the differentiation of mesenchymal stem cells into osteocytes, they are supplemented with, for instance, 100 nM dexamethasone, 10 mM beta-glycerophosphate and 0.05 mM of ascorbic acid-2-phosphate (osteogenic supplement).

The culture medium is changed every 3-4 days.
Construction of the Composite Graft In vitro Before they reach confluence, the cells are detached from the dish by enzymatic treatment, counted, suspended in a serum-free medium at a concentration of $5 \times 10^6$/ml, and loaded into the materials, for example by the bland vacuum technique.

MSCs exposed to TGF-beta 1 were loaded into a sponge made of a hyaluronan derivative (HYAFF®-11) for the construction of the cartilage component of the composite graft, and MSCs exposed to osteogenic supplement were loaded into a porous calcium phosphate ceramic component for bone formation. Cell-loaded HYAFF-11 sponge and ceramic were assembled and joined together with fibrin glue to form a composite osteochondral graft. Said graft is incubated at 37° C. for 30 minutes and then grafted subcutaneously into the backs of syngeneic rats in special pockets made with a blunt instrument.

The animals are sacrificed three to six weeks later and the material is histologically processed.

Results

The composite material remains in one piece after in vivo grafting and is encapsulated in a thin layer of fibrous tissue that can easily be removed. There are no signs of the cartilage part and the bone part having become separated in any way.

Three weeks later, fibrocartilage tissue can be seen in the empty spaces of the matrix based on hyaluronic acid derivatives, especially in the peripheral part of the material. After six weeks (FIG. 1), well-organised fibrocartilage is distributed through the material, that is partially absorbed. The chondrocytes are located in lacunae surrounded by extracellular matrix. In the extracellular matrix of the cartilage tissue, only type II cartilage can be seen.

Three weeks after grafting, bone tissue can be seen in the pores in the ceramic material, and the quantity of this tissue increases with time.

The fibrin glue has been completely absorbed after six weeks.

The separate formation of cartilage and bone can be seen in the two materials: neither the bone tissue nor the cartilage crosses the tidemark between the two materials. At the same time, the two materials form a structurally integrated composite material thanks to the presence of fibrous tissue and collagen fibres that do cross the tidemark.

This suggests that it is possible to construct a composite graft of engineered, osteochondral tissue using different materials that act as a scaffold for the chondrogenic and osteogenic differentiation of mesenchymal cells, thanks to their specific chondro-inductive and osteo-inductive potentials.

The invention being thus described, it is clear that this experiment can be modified in various ways with regard to the working conditions and methods. Such modifications are not to be considered as divergences from the spirit and purpose of the invention, and any modification that would be evident to an expert in the field comes within the scope of the following claims.

The invention claimed is:

1. A biocompatible, composite osteochondral graft comprising:
   (a) a first portion which is specifically chondro-inductive in the form of a non-woven fabric, membrane or sponge comprising a three-dimensional scaffold of at least one hyaluronic acid derivative;
   (b) a second portion which is specifically osteo-inductive comprising a porous, three-dimensional scaffold comprising a ceramic material;
   wherein said first and second portions are separate but joined together with a natural, synthetic or semi-synthetic adhesive that is biocompatible, whereby implantation of said osteochondral graft in vivo stimulates formation of cartilage tissue in said first portion and formation of bone tissue in said second portion without penetration of said cartilage tissue in said second portion and without penetration of said bone tissue in said first portion.

2. The osteochondral graft according to claim 1, wherein said adhesive is a fibrin glue.

3. The osteochondral graft according to claim 1, wherein the hyaluronic acid derivatives comprises hyaluronic acid esters wherein part or all of the carboxy functions are esterified with alcohols of the aliphatic, aromatic, arylaliphatic, cycloaliphatic or heterocyclic series.

4. The osteochondral graft according to claim 3, wherein the hyaluronic acid esters comprise autocrosslinked esters of hyaluronic acid, wherein part or all of the carboxy groups are esterified with the alcoholic functions of the same polysaccharide chain or of other chains.

5. The osteochondral graft according to claim 3, wherein the hyaluronic acid esters comprise crosslinked compounds of hyaluronic acid wherein part or all of the carboxy groups are esterified with polyalcohols of the aliphatic, aromatic, arylaliphatic or heterocyclic series, crosslinked by means of spacer chains.

6. The osteochondral graft according to claim 3, wherein the hyaluronic acid esters comprise hemiesters of succinic acid or heavy metal salts of the hemiester of succinic acid with hyaluronic acid or with partial or total esters of hyaluronic acid.

7. The osteochondral graft according to claim 3, wherein the hyaluronic acid esters comprise sulphated derivatives of hyaluronic acid.

8. The osteochondral graft according to claim 3, wherein the hyaluronic acid esters comprise amides of hyaluronic acid or derivatives thereof.

9. The osteochondral graft according to claim 1, wherein the ceramic material comprises a calcium phosphate or a calcium sulphate.

10. The osteochondral graft according to claim 9, wherein the ceramic material comprises at least one member selected from the group consisting of hydroxyapatite, tricalcium phosphate, and calcium sulphates.

11. The osteochondral graft according to claim 10, further comprising biocompatible metal particles or polymers.

12. The osteochondral graft according to claim 1, wherein the first and second portions further comprise at least one pharmacologically active ingredient selected from the group consisting of antibiotics, disinfectants and antiseptics, antivirals, antimicrobials and antifungal agents, nonsteroid and steroid anti-inflammatory drugs, cytostatic agents, cytotoxic agents, anaesthetics, and anticancer agents.

13. The osteochondral graft according to claim 1 or 12, wherein the first and second portions further comprise at least one biologically active ingredient that favors the adhesion of cells to the biocompatible, composite osteochondral graft selected from the group consisting of growth factors, bone morphogenic proteins, osteogenic proteins, growth hormones, vitamins, and glucosamine sulphate.

14. The osteochondral graft according to claim 1, wherein said first and second portions further comprise at least one osteo-chondrogenic cell selected from the group consisting of osteocytes, chondrocytes, bone marrow cells and mesenchymal stem cells.

15. The osteochondral graft according to claim 14, wherein the cells are autologous, allologous or xenologous.

16. A biocompatible, composite osteochondral graft comprising:
   (a) a first portion which is specifically chrondro-inductive, in the form of a non-woven fabric, membrane or sponge comprising a three-dimensional scaffold comprising (i) at least one hyaluronic acid ester wherein part or all of the carboxy functions are esterified with alcohols of the aliphatic, aromatic, arylaliphatic, cycloaliphatic or heterocyclic series or (ii) at least one autocrosslinked esters of hyaluronic acid, wherein part or all of the carboxy groups are esterified with the alcoholic functions of the same polysaccharide chain or of other chains;

(b) a second portion which is specifically osteo-inductive comprising a porous, three-dimensional scaffold comprising a ceramic material of a calcium phosphate or a calcium sulphate;

wherein said first and second portions are separate but joined together with a natural, synthetic or semi-synthetic adhesive that is biocompatible, whereby implantation of said osteochondral graft in vivo stimulates formation of cartilage tissue in said first portion and formation of bone tissue in said second portion without penetration of said cartilage tissue in said second portion and without penetration of said bone tissue in said first portion.

17. The osteochondral graft according to claim 16, wherein said first portion is in the form of a non-woven fabric comprised of the benzyl ester of hyaluronic acid.

18. The osteochondral graft according to claim 16, wherein said first portion is in the form of a non-woven fabric comprised of cross-linked hyaluronic acid.

19. The osteochondral graft according to claim 16, wherein said first portion is in the form of a sponge comprised of the benzyl ester of hyaluronic acid.

20. The osteochondral graft according to claim 16, wherein said first portion is in the form of a sponge comprised of cross-linked hyaluronic acid.

21. The osteochondral graft according to claim 16, wherein the first and second portions further comprise at least one pharmacologically active ingredient selected from the group consisting of antibiotics, disinfectants and antiseptics, antivirals, antimicrobials and antifungal agents, nonsteroid and steroid anti-inflammatory drugs, cytostatic agents, cytotoxic agents, anaesthetics, and anticancer agents.

22. The osteochondral graft according to claim 16 or 21, wherein the first and second portions further comprise at least one biologically active ingredient selected from the group consisting of substances that favor the adhesion of cells to the biomaterial, growth factors, bone morphogenic proteins, osteogenic proteins, growth hormones, vitamins, and glucosamine sulphate.

23. The osteochondral graft according to claim 16, wherein said first and second portions further comprise at least one osteo-chondrogenic cell selected from the group consisting of osteocytes, chondrocytes, bone marrow cells and mesenchymal stem cells.

24. A biocompatible, composite osteochondral graft comprising:

(a) a first portion which is specifically chondro-inductive in the form of a non-woven fabric, membrane or sponge comprising a three-dimensional scaffold comprising (i) at least one hyaluronic acid ester wherein part or all of the carboxy functions are esterified with alcohols of the aliphatic, aromatic, arylaliphatic, cycloaliphatic or heterocyclic series or (ii) at least one autocrosslinked esters of hyaluronic acid, wherein part or all of the carboxy groups are esterified with the alcoholic functions of the same polysaccharide chain or of other chains;

(b) a second portion which is specifically osteo-inductive comprising a porous, three-dimensional scaffold comprising a ceramic material of a calcium phosphate or a calcium sulphate;

wherein said first and second portions are separate but joined together with a biocompatible, natural, synthetic or semi-synthetic adhesive, whereby implantation of said osteochondral graft in vivo stimulates formation of cartilage tissue without stimulating formation of bone tissue in said first portion and stimulates formation of bone tissue without stimulating formation of cartilage tissue in said second portion; without penetration of said cartilage tissue in said second portion and without penetration of said bone tissue in said first portion.

25. The osteochondral graft according to claim 24, wherein said first portion is in the form of a non-woven fabric comprised of the benzyl ester of hyaluronic acid.

26. The osteochondral graft according to claim 24, wherein said first portion is in the form of a non-woven fabric comprised of cross-linked hyaluronic acid.

27. The osteochondral graft according to claim 24, wherein said first portion is in the form of a sponge comprised of the benzyl ester of hyaluronic acid.

28. The osteochondral graft according to claim 24, wherein said first portion is in the form of a sponge comprised of cross-linked hyaluronic acid.

* * * * *